(12) United States Patent
Maeda et al.

(10) Patent No.: US 6,720,185 B2
(45) Date of Patent: Apr. 13, 2004

(54) METHOD FOR ANALYSIS OF THE TEXTURAL STRUCTURE OF FOOD OF A MULTI-COMPONENT DISPERSION SYSTEM

(75) Inventors: Tatsurou Maeda, Iruma-gun (JP); Masaharu Yamada, Iruma-gun (JP); Kouji Takeya, Iruma-gun (JP)

(73) Assignee: Nisshin Seifun Group Inc., Tokyo (JP)

( * ) Notice: Subject to any disclaimer, the term of this patent is extended or adjusted under 35 U.S.C. 154(b) by 0 days.

(21) Appl. No.: 10/223,366

(22) Filed: Aug. 20, 2002

(65) Prior Publication Data

US 2003/0180956 A1 Sep. 25, 2003

(30) Foreign Application Priority Data

Feb. 13, 2002 (JP) .......................................... 2002-034776
Mar. 29, 2002 (JP) .......................................... 2002-094950

(51) Int. Cl.$^7$ .......................... G01N 33/02; G01N 21/76
(52) U.S. Cl. .......................... 436/20; 436/164; 436/172
(58) Field of Search .......................... 436/20–24, 164, 436/172

(56) References Cited

U.S. PATENT DOCUMENTS

| | | | | |
|---|---|---|---|---|
| 3,936,271 A | * | 2/1976 | Statter .......................... | 436/20 |
| 4,007,632 A | * | 2/1977 | Segars .......................... | 73/78 |
| 5,410,021 A | * | 4/1995 | Kampen .......................... | 430/372 |
| 5,658,798 A | * | 8/1997 | Bertin et al. .......................... | 436/3 |
| 6,001,655 A | * | 12/1999 | Spadaro et al. .......................... | 436/21 |

* cited by examiner

Primary Examiner—Maureen M. Wallenhorst
(74) Attorney, Agent, or Firm—Oblon, Spivak, McClelland, Maier & Neustadt, P.C.

(57) ABSTRACT

A method for analysis of the textural structure of a food of a multi-component dispersion system, in which a food of a multi-component dispersion system is stained with a fluorescent dye, and observing the stained food within a wavelength range lower than the value calculated by subtracting 40 nm from the maximum absorption wavelength of the employed fluorescent dye. The method enables image analysis through stereoscopic visualization of the textural structure of a food of a multi-component dispersion system.

12 Claims, 1 Drawing Sheet

[Fig. 1]
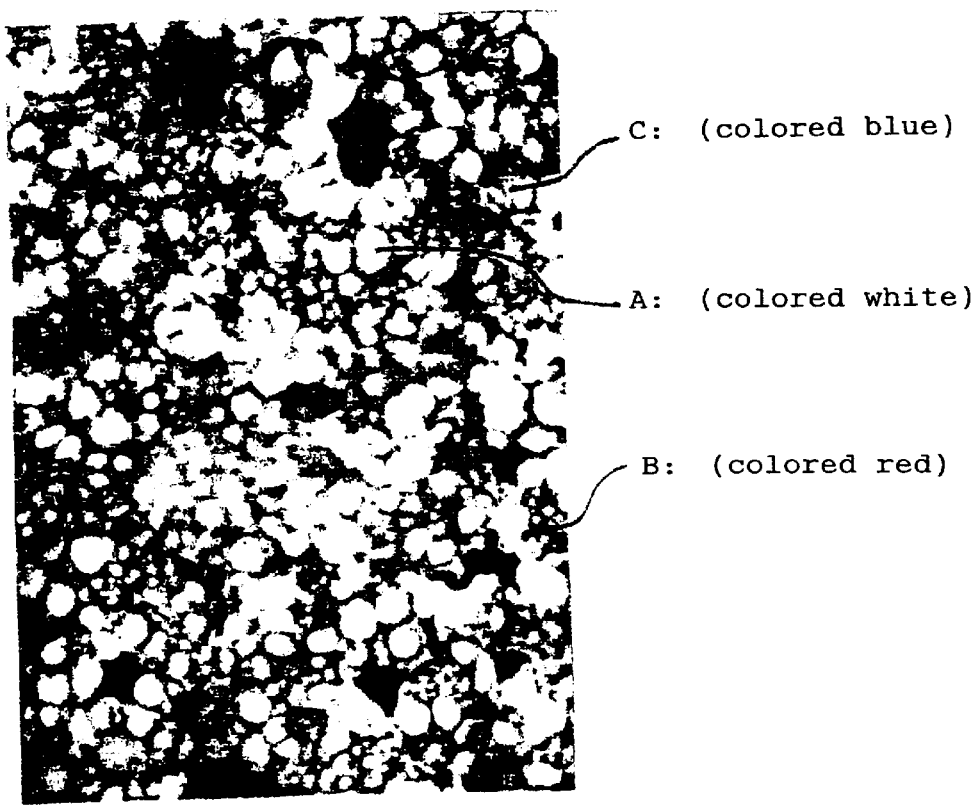

METHOD FOR ANALYSIS OF THE TEXTURAL STRUCTURE OF FOOD OF A MULTI-COMPONENT DISPERSION SYSTEM

TECHNICAL FIELD

The present invention relates to a method for stereoscopic analysis of the textural structure of a food of a multi-component dispersion system, the food containing at least one component (i.e., member; the same applies hereafter) selected from among starches, proteins, and lipids.

BACKGROUND ART

Starches, proteins, and lipids are accepted to be three major nutrient groups of foods. Wheat flour or rice is a principal raw material of a certain class of processed foods including breads, noodles, cooked rice, confectioneries, and tenpura, and taste and oral sensation imparted by a food are considered to be greatly affected by the form of the three major nutrients contained in the food. Conventionally, taste and oral sensation of the above foods have been evaluated through sensory testing. In recent years, attempts have been made to elucidate the textural structure of food through use of apparatus and devices, and on the basis of the thus-clarified textural structure, to determine oral sensation, etc. However, observation of the textural structure through use of such apparatus and devices does not necessarily lead to satisfactory evaluation, in that borders between respective components are sometimes unclear, or captured images are planar and non-stereoscopic.

For example, in the case of observation through an electron microscope, an electron beam is applied to a specimen and reflected electrons are detected for observation of shapes of the specimen (scanning electron microscopy), or, alternatively, differences between the information provided by electrons that have penetrated the sample and the information provided by electrons that have not penetrated the sample are detected for observation of shapes of the specimen (transmission electron microscopy). These methods enable observation of a specimen at very high resolution, but since these methods do not permit staining of samples, discrimination of specific components is difficult, thereby preventing structural analysis of borders between the components.

In the case of observation through an optical microscope, specific components of a specimen are stained before observation of the specimen. In this case also, border portions are unclear. When multi-staining is performed, some extent of segmentation by color is possible, but staining specificity is small and dyes overlap, substantially preventing discernment of the textural structure.

A confocal laser microscope can concentrate intense light that travels along a highly straight path to a single point through use of laser light. Using such laser light, the confocal laser microscope can provide correctly focused images and sectional images of deep focal depths, whereby images of high contrast can be obtained. However, confocal laser microscopy does not permit staining of specimens, and thus discrimination of specific components is difficult, whereby structural analysis of borders between the components becomes difficult.

The present inventors have performed extensive studies regarding image analysis methodology that enables clear, definite discernment with respect to the complex textural structure of food of a multi-component dispersion system, the food containing starches, proteins, and lipids, thereby leading to completion of the invention.

DISCLOSURE OF THE INVENTION

Accordingly, the present invention is directed to a method for analysis of the textural structure of a food of a multi-component dispersion system, characterized by comprising staining food containing at least one component selected from among starches, proteins, and lipids with at least one species of a fluorescent dye, and observing the stained food within a wavelength range lower than the value calculated by subtracting 40 nm from the maximum absorption wavelength of the employed fluorescent dye, preferably within a wavelength range lower than the value calculated by subtracting 50 nm from the maximum absorption wavelength of the employed fluorescent dye, more preferably within a wavelength range lower than the value calculated by subtracting 70 nm from the maximum absorption wavelength of the employed fluorescent dye.

The present invention is also directed to a method for analysis of the textural structure of a food of a multi-component dispersion system, characterized by comprising staining food containing at least one component selected from among starches, proteins, and lipids with at least one species of a fluorescent dye, observing the stained food at two or more different wavelengths which fall within a wavelength range lower than the value calculated by subtracting 40 nm from the maximum absorption wavelength of the employed fluorescent dye, and synthesizing at least two obtained images (hereinafter referred to as an image synthesis method).

BRIEF DESCRIPTION OF THE DRAWING

FIG. 1 is a photograph of the texture of Cookie dough observed under a fluorescent microscope.

BEST MODES FOR CARRYING OUT THE INVENTION

The method of the present invention will next be described.

A texture sample of food containing at least one component selected from among starches, proteins, and lipids (hereinafter referred to as food of a multi-component dispersion system) is prepared. The specimen can be prepared through freezing fixation, immersion fixation, microwave fixation, or through a similar method.

Next, the freezing fixation method will be described.

A food of a multi-component dispersion system is frozen on a cooling stage of a microtome for fixation. The freeze-fixed specimen is sliced to a predetermined thickness. Each of the slices is placed on a slide glass, brought to dryness by use of a heater, and fixed. Separately, a fluorescent dye solution is prepared, and the solution is allowed to react with the specimen slice for a predetermined period of time (for example, 1 to 30 minutes; when reaction for a longer time is desired, 1 to 3 hours), followed by drying. The dried specimen slice is embedded in soft Canadian balsam, whereby a specimen is prepared.

When a specimen slice is stained with a plurality of fluorescent dyes for preparation of a textural sample, a cycle consisting, in series, of reaction with a fluorescent dye, drying, reaction with another fluorescent dye, and drying is repeated.

In immersion fixation, a food of a multi-component dispersion system is immersed in a formalin solution (about 10%) or a glutaraldehyde solution (about 5%) for 12 to 24 hours. Subsequently, the resultant food of a multi-component dispersion system is washed with running water for several hours (e.g., 1 to 12 hours). The washed food of a multi-component dispersion system is dehydrated, followed by sequential immersion in 80% ethanol, 95% ethanol, 99.5% ethanol, and 100% ethanol, for 2 to 4 hours each immersion step. Next, the food of a multi-component dispersion system is immersed in a solution of xylene—soft paraffin for 12 hours for burying the food in the solution. The food-enclosing paraffin is fixed onto a table. The thus-fixed food of a multi-component dispersion system is sliced to a predetermined thickness by use of a microtome. The slices are floated on a water bath (35–40°) so that wrinkles are smoothed out, and individually scooped onto a slide glass for drying. Separately, a fluorescent dye solution is prepared, and the solution is allowed to react with each of the specimen slices for a predetermined period of time (for example, 1 to 30 minutes; when reaction for a longer time is desired, 1 to 3 hours), followed by drying. The dried specimen slice is embedded in soft Canadian balsam, whereby a textural sample is prepared.

When a specimen slice is stained with a plurality of fluorescent dyes, similar to the case of freezing fixation, the slice is subjected to reaction with a fluorescent dye, drying, reaction with another fluorescent dye, and to drying, and this procedure is repeated, whereby multi-staining can be performed.

In the case of microwave fixation, for example, a food of a multi-component dispersion system is immersed, for example, in a glutaraldehyde solution for 12 to 24 hours, and then is irradiated with microwave energy for 10 to 60 seconds for fixation. Subsequent steps are similar to those described in relation to the immersion fixation, whereby a textural sample can be obtained.

According to the method of the present invention, firstly, the aforementioned textural sample—i.e., a food sample containing at least one component selected from among starch, protein, and lipid—is stained with at least one fluorescent dye.

In the method of the present invention, the fluorescent dye which may be employed as a staining agent include fluorescein isothiocyanate, eosin isothiocyanate, Lucifer Yellow CH, Resorfin, tetramethylrhodamine isothiocyanate, coumarin maleimide, 7-amino-4-methylcoumarin-3-acetic acid, fluorescamine, dansyl chloride, dansylhydrazine, Acid Green, Acridine Orange, Acridine Yellow, Congo Red, Acid Fuchsine, Nile Blue, Fast Green FCF, calcein, Calcein Blue, acriflavine, Evans Blue, Rhodamine 123, Sudan black B, periodic acid Schiff, Basic Pararosaniline, Pararosaniline Acetate, Basic Rubin, Magenta III, Aniline Blue, Alphazurin A, Alphazurin FG Patent Blue VF, tri-(p-aminophenyl) amine, and tri(p-isothiocyanatophenyl)amine.

Of the above fluorescent dyes, those capable of staining specifically starch include Congo Red and periodic acid Schiff; those capable of staining specifically proteins include fluorescamine, Acid Fuchsine, Basic Para Rosaniline, Para Rosaniline Acetate, Basic Rubin, Magenta III, Aniline Blue, Alphazurin A, Alphazurin FG, Patent Blue VF, tri-(p-aminophenyl)amine, and tri(p-isothiocyanatophenyl)amine; and those capable of staining specifically lipids include Nile Blue and Sudan Black B.

According to the present invention, staining of a food is performed through use of at least one fluorescent dye, or alternatively through use of two or more fluorescent dyes (called multi-staining). The fluorescent dye(s) may be used in combination with non-fluorescent dye(s). An example non-fluorescent dye is iodine.

Subsequently, the food stained with a fluorescent dye is observed within a wavelength range lower than the value calculated by subtracting 40 nm from the maximum absorption wavelength of the employed fluorescent dye, preferably within a wavelength range lower than the value calculated by subtracting 50 nm from the maximum absorption wavelength of the employed fluorescent dye, more preferably within a wavelength range lower than the value calculated by subtracting 70 nm from the maximum absorption wavelength of the employed fluorescent dye.

According to the aforementioned image synthesis method, which is another method falling within the present invention, the stained food is observed at two or more different wavelengths which fall within a wavelength range lower than the value calculated by subtracting 40 nm from the maximum absorption wavelength of the employed fluorescent dye, preferably within a wavelength range lower than the value calculated by subtracting 50 nm from the maximum absorption wavelength of the employed fluorescent dye, more preferably within a wavelength range lower than the value calculated by subtracting 70 nm from the maximum absorption wavelength of the employed fluorescent dye. When observation is performed within a wavelength range higher than the value calculated by subtracting 40 nm from the maximum absorption wavelength of the employed fluorescent dye, fluorescence intensity increases to such a level that does not permit easy discrimination of components, thereby failing to attain the objects of the invention.

In the present invention, "observation" is performed through use of visible light, or within an infrared or ultraviolet wavelength range, depending on the species of the fluorescent dye employed. When observation is performed within an infrared or ultraviolet wavelength range, a specific observation apparatus is employed, to thereby transform observed data into electrical signals, which are then processed with a computer.

Examples of light sources which may be used for fluorescence observation in the present invention include a mercury lamp (100V), a mercury lamp (200V), a xenon lamp (75V), a xenon lamp (150V), a halogen lamp (12V 100W), and a tungsten lamp (6V 30W). Other than these lamps, there may be employed excitation light sources, such as a xenon lamp (250–1,000 nm), a tungsten lamp (250–1,000 nm), a Cr:LiSAF lamp (430 nm), a helium-cadmium laser (325, 442 nm), an argon laser (442 nm), argon ion laser (488, 514 nm), Nd:YAG laser (532 nm), helium neon laser (543, 594, 633 nm), a krypton ion laser (568, 647 nm).

In the present invention, when the textural structure of a food of a multi-component dispersion system is analyzed, normally, fluorescence is observed. In this case, if phase contrast is used in combination, the textural structure can be observed more stereoscopic. Phase contrasting is available in the bright field observation, phase contrast observation, and differential interference observation, and in particular, use in combination of phase contrast observation and differential interference observation is preferred.

Examples of the filters which may be used in the aforementioned fluorescence observation include excitation filters, dichroic filters, absorption filters, and mirror units comprising a set of these filters. Specific examples of such mirror units include U-MWU (an excitation filter (330–385 nm), an absorption filter (420 nm), and an absorption filter (400 nm)], U-MWIB (an excitation filter (460–490 nm), an absorption filter (515 nm), and an absorption filter (505 nm)), U-MWIG (an excitation filter (520–550 nm), an absorption filter (580 nm), and an absorption filter (565 nm)), U-MWIY (an excitation filter (545–580 nm), an absorption filter (610 nm), and an absorption filter (600 nm)) (produced by Olympus Optical Co., Ltd.).

When the aforementioned fluorescence observation and bright-field observation are used in combination, preferably, the luminous transmittance of light from the illumination lamp is suppressed to 6% or less. In this case, ND filters which may be employed include an LBD filter (produced by Olympus Optical Co., Ltd.), an ND25 filter (produced by Olympus Optical Co., Ltd.), and an ND6 filter (produced by Olympus Optical Co., Ltd.).

According to the image synthesis method of the present invention, the aforementioned observation must be made at two or more points in wavelength which fall within a wavelength range lower than the value calculated by subtracting 40 nm from the maximum absorption wavelength of the employed fluorescent dye.

Next, fluorescence observation in the image synthesis method of the present invention will be described.

When a textural sample of a food of a multi-component dispersion system is stained with a fluorescent dye A ($\lambda max_a$), observation is performed at a wavelength "a–45" (nm) and "a–60" (nm).

Separately, in the case where a plurality of fluorescent dyes are used to stain a textural sample of a food of a multi-component dispersion system, when fluorescence observation is performed by use of, for example, a fluorescent dye B ($\lambda max_b$) and a fluorescent dye C ($\lambda max_c$), any of the following combinations of observation may be performed: observation at "b–50" (nm) and "b–80" (nm); "c–60" (nm) and "c–70" (nm); "b–50" (nm) and "c–60" (nm); "b–80" (nm) and "c–60" (nm); and "b–50" (nm), "b–80" (nm), "c–60" (nm), and "c–60" (nm)

A plurality of images obtained from observation at a plurality of points in wavelength are superposed one on another, to thereby obtain a synthesized image, and the thus obtained synthesized image is examined.

EXAMPLES

The present invention will next be described in more detail by way of examples, which should not be construed as limiting the invention thereto.

Example 1

| Cookie dough having the following formulation was used: | |
|---|---|
| Margarine | 55 weight parts |
| White soft sugar | 45 |
| Common salt | 0.3 |
| Whole egg | 18 |
| Wheat flour | 100 |
| BP | 0.5 |
| Sodium bicarbonate | 0.25 |
| Ammonium carbonate | 0.25 |

This Cookie dough was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a protein-staining dye, Acid Fuchsine ($\lambda_{max}$=545 nm). The stained specimen was observed under an optical microscope (BX50, produced by Olympus Optical Co., Ltd.) in the bright field (transmittance 1.5%) and also through use of a fluorescent filter shown in Table 1.

Evaluation was performed by 10 panelists, on the basis of the evaluation standards shown in Table 2. The results of the evaluation are shown in Table 1.

TABLE 1

| Excitation filter | U-MWU | U-MWIG (control) |
|---|---|---|
| Excitation wave length (nm) | 330–385 | 520–550 |
| Wave length of fluorescent filter (nm) | 420 | 580 |
| Observation (fluorescent field + bright field) | 4.6 | 1.6 |

TABLE 2

| Point | Evaluation standards |
|---|---|
| 5 | Two or more components from among starches, proteins, etc. can be clearly distinguished and observed stereoscopically. |
| 4 | Two or more components from among starches, proteins, etc. can be clearly distinguished. |
| 3 | Two or more components from among starches, proteins, etc. can be distinguished. |
| 2 | Only one component from among starches, proteins, etc. can be distinguished. |
| 1 | Discrimination is impossible. |

Example 2

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a lipid-staining dye, Nile Blue ($\lambda_{max}$=625 nm). The stained specimen was observed under an optical microscope (BX50, produced by Olympus Optical Co., Ltd.) in the bright field (transmittance 6%) and also through use of a fluorescent filter shown in Table 3.

Evaluation was performed in a manner similar to that described in connection with Example 1. The results of the evaluation are shown in Table 3.

TABLE 3

| Excitation filter | U-MWU | U-MWIG | U-MWIY (control) |
|---|---|---|---|
| Excitation wave length (nm) | 330–385 | 520–550 | 545–585 |
| Wave length of fluorescent filter (nm) | 420 | 580 | 610 |
| Observation (fluorescent field + bright field) | 3.8 | 3.5 | 1.2 |

Example 3

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a starch-staining dye, Congo Red ($\lambda_{max}$=497 nm). The stained specimen was observed under an optical microscope (BX50, produced by Olympus Optical Co., Ltd.) in the bright field (transmittance 1.5%) and also through use of a fluorescent filter shown in Table 4.

Evaluation was performed in a manner similar to that described in connection with Example 1. The results of the evaluation are shown in Table 4.

TABLE 4

| Excitation filter | U-MWU | U-MWIB (control) |
|---|---|---|
| Excitation wave length (nm) | 330–385 | 460–490 |
| Wave length of fluorescent filter (nm) | 420 | 515 |
| Observation (fluorescent field + bright field) | 4.0 | 1.5 |

Example 4

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a non-starch-staining dye, Fast Green FCF ($\lambda_{max}$=622 nm). The stained specimen was observed under an optical microscope (BX50, produced by Olympus Optical Co., Ltd.) in the bright field (transmittance 1.5%) and also through use of a fluorescent filter shown in Table 5.

Evaluation was performed in a manner similar to that described in connection with Example 1. The results of the evaluation are shown in Table 5.

TABLE 5

| Excitation filter | U-MWU | U-MWIG | U-MWIY (control) |
|---|---|---|---|
| Excitation wave length (nm) | 330–385 | 520–550 | 545–580 |
| Wave length of fluorescent filter (nm) | 420 | 580 | 610 |
| Observation (fluorescent field + bright field) | 4.1 | 3.5 | 1.6 |

Example 5

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a protein-staining dye, Acid Fuchsine ($\lambda_{max}$=545 nm). The stained specimen was observed under a fluorescence microscope (BX50, produced by Olympus Optical Co., Ltd.) through use of a fluorescent filter shown in Table 6. Separately, the specimen was observed by combination of a fluorescent filter and either of phase contrast or differential interference contrast.

Evaluation was performed in a manner similar to that described in connection with Example 1. The results of the evaluation are shown in Table 6.

TABLE 6

| Excitation filter (nm) | U-MWU (330–385) | U-MWIG (520–550) (control) |
|---|---|---|
| Wave length of fluorescent filter (nm) | 420 | 580 |
| Observation (fluorescent field) | 4.6 | 1.1 |
| Observation (fluorescent field + phase contrast) | 4.7 | 1.2 |
| Observation (fluorescent field + differential interference contrast) | 4.7 | 1.3 |

Example 6

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a lipid-staining dye, Nile Blue ($\lambda_{max}$=625 nm). The stained specimen was observed under a fluorescence microscope (BX50, produced by Olympus Optical Co., Ltd.) through use of a fluorescent filter shown in Table 7. Separately, the specimen was observed by combination of a fluorescent filter and either of phase contrast or differential interference contrast.

Evaluation was performed in a manner similar to that described in connection with Example 1. The results of the evaluation are shown in Table 7. Moreover, a photograph of the texture observed by use of a fluorescent filter (420 nm) and an excitation filter U-MWU is shown in FIG. 1. As shown in FIG. 1, the particles (A=starch (white), B=protein (red), and C=lipid (blue)) can be clearly distinguished from one another.

TABLE 7

| Excitation filter (nm) | U-MWU (330–385) | U-MWIB (460–490) | U-MWIY (545–580) (control) |
|---|---|---|---|
| Wave length of fluorescent filter (nm) | 420 | 515 | 610 |
| Observation (fluorescent field) | 3.8 | 3.5 | 1.2 |
| Observation (fluorescent field + phase contrast) | 4.0 | 3.8 | 1.3 |
| Observation (fluorescent field + differential interference contrast) | 4.1 | 3.9 | 1.0 |

Example 7

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a starch-staining dye, Congo Red ($\lambda_{max}$=497 nm). The stained specimen was observed under a fluorescence microscope (BX50, produced by Olympus Optical Co., Ltd.) through use of a fluorescent filter shown in Table 8. Separately, the specimen was observed by combination of a fluorescent filter and either of phase contrast or differential interference contrast.

Evaluation was performed in a manner similar to that described in connection with Example 1. The results of the evaluation are shown in Table 8.

TABLE 8

| Excitation filter (nm) | U-MWU (330–385) | U-MWIB (460–490) (control) |
|---|---|---|
| Wave length of fluorescent filter (nm) | 420 | 515 |
| Observation (fluorescent field) | 4.0 | 1.5 |
| Observation (fluorescent field + phase contrast) | 4.1 | 1.8 |
| Observation (fluorescent field + differential interference contrast) | 4.1 | 1.3 |

Example 8

Cookie dough having the same formulation as that in Example 1 was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a non-starch-staining dye, Fast Green FCF ($\lambda_{max}$=622 nm). The stained specimen was observed under a fluorescence microscope (BX50, produced by Olympus Optical Co., Ltd.) through use of a fluorescent filter shown in Table 9. Separately, the specimen was observed by combination of a fluorescent filter and either of phase contrast or differential interference contrast.

Evaluation was performed in a manner similar to that described in connection with Example 1. The results of the evaluation are shown in Table 9.

TABLE 9

| Excitation filter (nm) | U-MWU (330–385) | U-MWIB (460–490) | U-MWIY (545–580) (control) |
|---|---|---|---|
| Wave length of fluorescent filter (nm) | 420 | 515 | 610 |
| Observation (fluorescent field) | 4.1 | 3.5 | 1.6 |
| Observation (fluorescent field + phase contrast) | 4.3 | 3.6 | 1.4 |
| Observation (fluorescent field + differential interference contrast) | 4.4 | 3.8 | 1.3 |

Example 9, and Comparative Examples 1 to 3

Bread dough used herein had the following formulation.

| Wheat flour | 100 weight parts |
|---|---|
| Raw yeast | 2 |
| Yeast food (C oriental) | 0.1 |
| Common salt | 2 |
| Sugar | 6 |
| Skim milk powder | 2 |
| Shortening | 5 |
| Water | 70 |

This bread dough was rapidly frozen on a cooling stage. The frozen dough was sliced to a predetermined thickness by use of a microtome, and each of the slices was dry-fixed on a slide glass for a microscope, to thereby prepare a specimen. Subsequently, the specimen was stained with a protein-staining dye, Aniline Blue ($\lambda_{max}$=605 nm), and the stained specimen was dried sufficiently. The thus-obtained specimen was observed under a fluorescence microscope (BX51, produced by Olympus Optical Co., Ltd.) through use of a fluorescent filter shown in Table 10. Separately, the specimen was observed by combination of a fluorescent filter and either of phase contrast or differential interference contrast.

The images of the textural structure photographed during observation were superimposed one on the other, and the photograph of the synthesized image was observed by 10 panelists for evaluation, on the basis of the evaluation standards shown in Table 12. The results of the evaluation are shown in Table 11.

TABLE 10

| Filter | Wavelength (nm) |
|---|---|
| U-MWU (330–385) | 420 |
| U-MWIB (460–490) | 515 |
| U-MWIG (520–550) | 580 |
| U-MWIY (545–580) | 610 |

TABLE 11

| | Ex. 9 | Comp. Ex. 1 | Comp. Ex. 2 | Comp. Ex. 3 |
|---|---|---|---|---|
| Wave length of fluorescence (nm) at which observation was performed | 420 | 420 | 515 | 580 |
| Wave length of fluorescence (nm) at which observation was performed | 515 | 580 | 580 | 610 |
| Observation (fluorescent field) | 4.3 | 1.7 | 1.7 | 1.5 |
| Observation (fluorescent field + phase contrast) | 4.6 | 1.9 | 1.8 | 1.5 |
| Observation (fluorescent field + differential interference contrast) | 4.5 | 2.1 | 1.8 | 1.7 |

TABLE 12

| Point | Evaluation standards |
|---|---|
| 5 | Two or more components from among proteins, lipids, starches, etc. can be distinguished very clearly from one another, and the textural structure can be visualized stereoscopically. |
| 4 | Two or more components from among proteins, lipids, starches, etc. can be clearly distinguished from one another, and the textural structure can be visualized stereoscopically. |
| 3 | Two components from among proteins, lipids, starches, etc. can be distinguished from one another. |
| 2 | Only one component from among proteins, lipids, starches, etc. can be distinguished from other components. |
| 1 | Discrimination is impossible. |

Examples 10 to 12, and Comparative Examples 4 to 6

Noodle strand having the following formulation was used herein:

| | |
|---|---|
| Wheat flour | 100 parts |
| Water | 35 |
| Purified salt | 2 |

The noodle strands were immersion-fixed. The fixed noodle strands were freeze-fixed on a cooling stage. The freeze-fixed strands were sliced to a predetermined thickness by use of a microtome, and each of the slices was dry-fixed on a slide glass for a microscope, to thereby prepare a specimen. Subsequently, the specimen was stained with a protein-staining dye, Para Rosaniline Acetate ($\lambda_{max}$=545 nm), and the stained specimen was dried, after which the specimen was stained with a non-selective fluorescent dye, Fast Green FCF ($\lambda_{max}$=622 nm), and the stained specimen was dried.

The thus-obtained specimen was observed under a fluorescence microscope (BX51, produced by Olympus Optical Co., Ltd.) through use of a fluorescent filter shown in Table 10. Separately, the specimen was observed by combination of a fluorescent filter and either of phase contrast or differential interference contrast.

The images of the textural structure photographed during observation were superimposed one on the other, and the photograph of the synthesized image was observed for evaluation in a manner similar to that described in connection with Example 10. The results of the evaluation are shown in Table 13.

TABLE 13

| | Ex. 10 | Ex. 11 | Ex. 12 | Comp. Ex. 4 | Comp. Ex. 5 | Comp. Ex. 6 |
|---|---|---|---|---|---|---|
| Wave length of fluorescence (nm) at which observation was performed | 420 | 420 | 515 | 420 | 515 | 580 |
| Wave length of fluorescence (nm) at which observation was performed | 515 | 580 | 580 | 610 | 610 | 610 |
| Observation (fluorescent field) | 4.4 | 4.1 | 4.0 | 1.6 | 1.5 | 1.6 |
| Observation (fluorescent field + phase contrast) | 4.5 | 4.3 | 4.2 | 1.8 | 1.6 | 1.9 |
| Observation (fluorescent field + differential interference contrast) | 4.6 | 4.3 | 4.1 | 1.6 | 1.5 | 1.8 |

Example 13, and Comparative Examples 7 to 9

Tempura coating having the following formulation was used herein:

| | |
|---|---|
| Wheat flour | 100 weight parts |
| Common salt | 1 |
| Baking powder | 3 |
| Water | 170 |

This tempura coating was rapidly frozen on a cooling stage with a molder (Compound CTC, produced by Sankyo). The frozen product was sliced to a predetermined thickness by use of a microtome, and each of the slices was dry-fixed on a slide glass for a microscope, to thereby prepare a specimen. Subsequently, the specimen was stained with a lipid-staining dye, Sudan Black B ($\lambda_{max}$=598 nm), and the stained specimen was dried, after which the specimen was stained with a protein-staining dye, Acid Fuchsine ($\lambda_{max}$=545 nm), and the stained specimen was dried.

The thus-obtained specimen was observed under a fluorescence microscope (BX51, produced by Olympus Optical Co., Ltd.) through use of a fluorescent filter shown in Table 10. Separately, the specimen was observed by combination of a fluorescent filter and either of phase contrast or differential interference contrast.

The images of the textural structure photographed during observation were superimposed one on the other, and the photograph of the synthesized image was observed for evaluation in a manner similar to that described in connection with Example 10. The results of the evaluation are shown in Table 14.

TABLE 14

| | EX. 13 | Comp. Ex. 7 | Comp. Ex. 8 | Comp. Ex. 9 |
|---|---|---|---|---|
| Wave length of fluorescence (nm) at which observation was performed | 420 | 420 | 420 | 580 |
| Wave length of fluorescence (nm) at which observation was performed | 515 | 580 | 610 | 610 |
| Observation (fluorescent field) | 4.2 | 1.8 | 1.7 | 1.5 |
| Observation (fluorescent field + phase contrast) | 4.3 | 2.0 | 1.8 | 1.7 |
| Observation (fluorescent field + differential interference contrast) | 4.5 | 2.1 | 1.9 | 1.5 |

INDUSTRIAL APPLICABILITY

The present invention enables stereoscopic-image-based analysis of the textural structure of a food of a multi-component dispersion system, the food containing, among others, starches, proteins, and lipids.

What is claimed is:

1. A method for analysis of a textural structure of a food of a multi-component dispersion system, comprising the steps of staining food containing at least one component selected from the group consisting of starches, proteins, and lipids with at least one species of a fluorescent dye, and observing the stained food within a wavelength range lower than a value calculated by subtracting 40 nm from a maximum absorption wavelength of the fluorescent dye used to stain the food.

2. A method for analysis of a textural structure of a food of a multi-component dispersion system, comprising the steps of staining food containing at least one component selected from the group consisting of starches, proteins, and lipids with at least one species of a fluorescent dye, observing the stained food at two or more different wavelengths which fall within a wavelength range lower than a value calculated by subtracting 40 nm from a maximum absorption wavelength of the fluorescent dye used to stain the food, and synthesizing at least two images obtained therefrom.

3. The method according to claim 1, wherein the observation of the stained food is conducted within a wavelength range lower than the value calculated by subtracting 50 nm from the maximum absorption wavelength of the employed fluorescent dye.

4. The method according to claim 1, wherein the observation of the stained food is conducted within a wavelength range lower than the value calculated by subtracting 70 nm from the maximum absorption wavelength of the employed fluorescent dye.

5. The method according to claim 1, wherein the observation of the stained food is conducted by use of fluorescence observation and phase contrast observation in combination.

6. The method according to claim 1, wherein the observation of the stained food is conducted by use of fluorescence observation and phase contrast observation in combination, and by use of phase contrast observation as a phase contrasting means.

7. The method according to claim 1, wherein the observation of the stained food is conducted by use of fluorescence observation and phase contrast observation in combination, and by use of differential interference as a phase contrasting means.

8. The method according to claim 2, wherein the observation of the stained food is conducted within a wavelength range lower than the value calculated by subtracting 50 nm from the maximum absorption wavelength of the employed fluorescent dye.

9. The method according to claim 2, wherein the observation of the stained food is conducted within a wavelength range lower than the value calculated by subtracting 70 nm from the maximum absorption wavelength of the employed fluorescent dye.

10. The method according to claim 2, wherein the observation of the stained food is conducted by use of fluorescence observation and phase contrast observation in combination.

11. The method according to claim 2, wherein the observation of the stained food is conducted by use of fluorescence observation and phase contrast observation in combination, and by use of phase contrast observation as a phase contrasting means.

12. The method according to claim 2, wherein the observation of the stained food is conducted by use of fluorescence observation and phase contrast observation in combination, and by use of differential interference as a phase contrasting means.

* * * * *